United States Patent [19]

Schawl

[11] Patent Number: 4,750,479

[45] Date of Patent: Jun. 14, 1988

[54] PORTABLE SELF-APPLIED TRACTION DEVICE HAVING PLATES STRAPPED TO THIGHS

[76] Inventor: David L. Schawl, 1448-16th Ave., Camanche, Iowa 52730

[21] Appl. No.: 30,240

[22] Filed: Mar. 26, 1987

[51] Int. Cl.[4] .................... A61F 5/04

[52] U.S. Cl. .................... 128/75; 128/84 C

[58] Field of Search .................... 128/75, 69, 84 R, 84 C, 128/87 B, 78, 68

[56] References Cited

U.S. PATENT DOCUMENTS

| | | | |
|---|---|---|---|
| 1,508,892 | 9/1924 | Mikalsen | 128/75 |
| 1,614,641 | 1/1927 | Anderson | 128/75 |
| 3,134,379 | 5/1964 | Nightingale | 128/75 |
| 3,380,447 | 4/1968 | Martin | 128/75 |
| 3,556,090 | 1/1971 | Viel | 128/75 |
| 3,672,361 | 6/1972 | Fourneron | 128/71 |
| 3,799,156 | 3/1974 | Gurkin | 128/75 |
| 3,809,394 | 5/1974 | Hall | 272/80 |
| 4,039,183 | 8/1977 | Sakurada | 272/67 |
| 4,102,336 | 7/1978 | Wiener et al. | 128/75 |
| 4,383,524 | 5/1983 | Boger | 128/75 |
| 4,466,427 | 8/1984 | Granberg | 128/75 |
| 4,552,356 | 11/1985 | Brousseau | 272/137 |
| 4,641,637 | 2/1987 | Rosen | 128/75 |

*Primary Examiner*—Edgar S. Burr
*Assistant Examiner*—Tonya Lamb
*Attorney, Agent, or Firm*—Zarley McKee, Thomte, Voorhees & Sease

[57] ABSTRACT

A back preserver traction device which is comprised of holster-like plates for application of stretching pressure to a patient's back. The device comprises a pair of thigh conformable plates, each having an inner surface and an outer surface. A hand grip is mounted on the outer surface of each plate for grasping by a patient's hand and application of pressure along the spine, away from the head. The thigh-conformable plates are strapped together with a holding strap which surrounds the patient's waist, holding the plates against the thigh in a position similar to the position in which holsters are held.

9 Claims, 1 Drawing Sheet

PORTABLE SELF-APPLIED TRACTION DEVICE HAVING PLATES STRAPPED TO THIGHS

BACKGROUND OF THE INVENTION

This invention relates to a traction device. More particularly it relates to a traction device for applying as much pressure as a patient desires along the spine, away from the head and neck.

There is an ever increasing need for simple and economical traction devices which can be used to support an individual in a manner which applies pressure along the spine away from the head and neck in a generally downward direction, assuming the patient to be upright. There are, of course, many such devices on the market, but most are cumbersome, large and expensive. In view of the rather common occurrence of back problems amongst the population, there is therefore a real and continuing need for traction devices which can be used at home, which are simple and inexpensive, and which allow the patient to apply increasing or decreasing back pressure, at will.

There are good and anatomical physiological and mechanical reasons for the use of back traction, as opposed to surgery. Amongst those are reversing the gravitational effects of compaction on the spine, separating the joint spaces, and general decompression of the spine. It is a primary object of this invention to provide a simple, inexpensive device for home use by the patient to alleviate pressure and pain in the back.

Another object of the present invention is to provide a traction device which may be used at home by the patient which is simple and requires little or no mechanical expertise for use.

A further object of the invention is to provide a traction device which is comfortable and safe.

A still further object of the invention is to provide a traction device which allows the patient to completely control the traction along the long axis of the body by simply exerting more or less downward force with his or her arms.

Yet another object of the invention is to provide a traction device which is economical to manufacture, durable in use, safe, and easy to use.

The method and manner of accomplishing each of these objectives as well as others will be apparent to those skilled in the art.

SUMMARY OF THE INVENTION

A traction device which is comprised of a pair of holster-like plates for application of stretching traction along the long axis of the spine. The device comprises a pair of thigh-conformable plates having an inner surface and an outer surface. Preferably the inner surface is padded. Mounted to the outer surface is a hand grip for grasping by the patient's hand. Thus, the patient can simply exert a downward pressure by application of such forces from the arm and hands which stretches the spine away from the general direction of the neck, along its long axis. The pair of holster-like plates are held in position by a strap which surrounds the patient's waist and holds each of the plates in a general position of a hip holster adjacent each outer thigh of the patient.

DETAILED DESCRIPTION OF THE INVENTION

Figure 5:
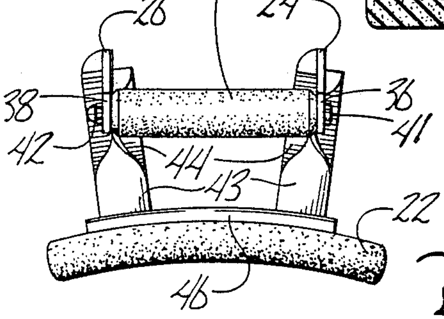
FIG. 5 is a top end view of the device.

The numeral 10 generally designates one of the holster-like plates of this invention, while the numeral 12 designates a patient and the numerals 14 and 16 designate the exterior rounded surface of the patient's thighs. The holster-like plate 10 includes a thigh-conformable plate 15 which has an outer surface 18 and an inner surface 20. Inner surface 20 is preferably covered with padded material 22. Padded material 22 can be made of a variety of polymeric plastic materials which are non-skin-irritable and well within the skill of the art. The precise pad composition employed does not form a part of the invention, independent from its use with the support plates. As depicted in FIG. 5, the inner surface of the support plate 15 is curved so that its curvature roughly corresponds to the outer surface of the patient 12's thighs 14 and 16 to allow conformable fitting and comfort.

The exterior or outer surface of each plate has attached thereto a pair of grip support straps 24 and 26. Positioned between grip support straps 24 and 26 is a hand grip 27. Hand grip 27 as depicted is covered with additional padded polymeric plastic material of like composition to that designated at 22. Straps 24 and 26 are mounted at their lower ends 28 and 30, respectively, to plate 15. The straps extend generally upwardly and are bent at corners 32 and 34 and from corners 32 and 34 extend generally slightly downwardly and inwardly towards the upper ends thereof, 36 and 38. Each of the straps has a plurality of spaced-apart aperatures 40, so that grip 27 may be adjustably secured in various positions along the straps 24 and 26 by means of bolts 41 and 42.

It is preferred that straps 24 and 26 extend downwardly and inwardly towards their top end in order to directionally transmit downward pressure towards the thigh and to prevent rotational forces from being exerted against the holster-like plates.

Figure 4:
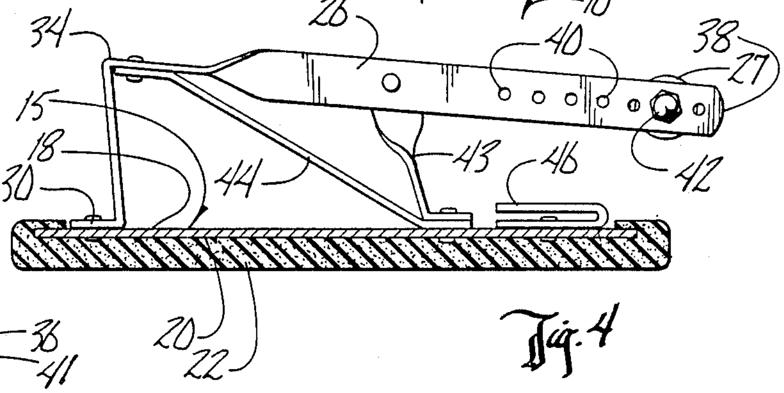
FIG. 4 is a sectional view along line 4—4 of FIG. 3.

For further support of the grip supports 24 and 26, as best depicted in FIG. 4, there are shown an intermediate support leg 43 and a diagonal support leg 44. The straps 24 and 26 as well as the intermediate support legs 43 and 44 may be secured in position by riveting or other suitable fastening means.

At the upper end of each holster-like plate on the outer side thereof is positioned a belt or belt support clip 46. Waist belt 48 is secured around the waist of patient 12 and extends through the belt support clip 46 of each holster-like plate 10.

Figure 1:
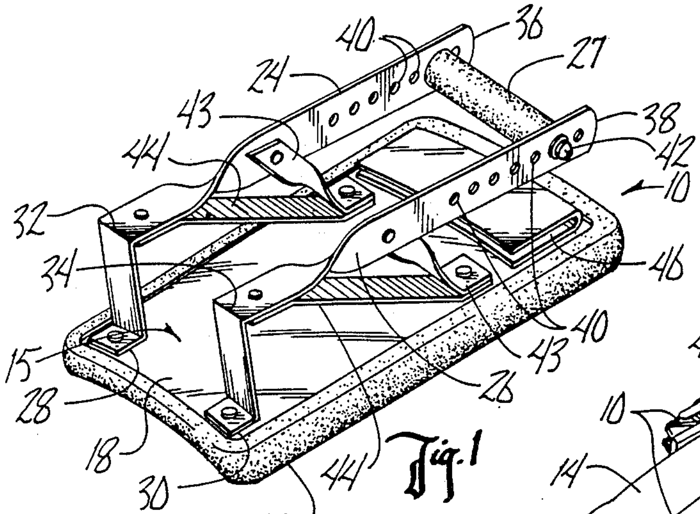
FIG. 1 is an elevated perspective view of one of the holster plates of this invention.
Figure 2:
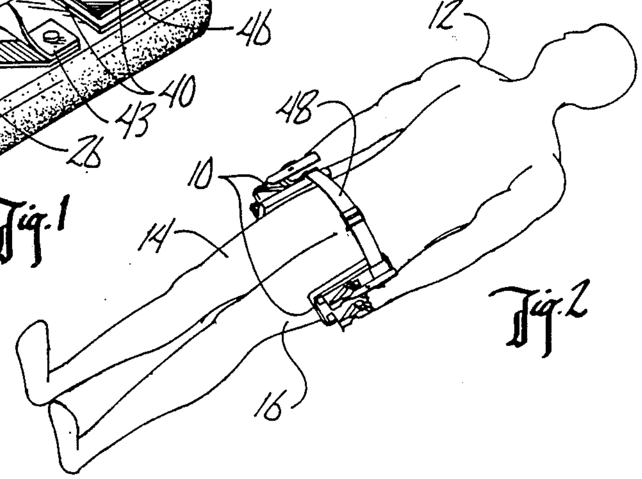
FIG. 2 shows a patient lying on his back, presumably on the floor, with the device in its use position.
Figure 3:
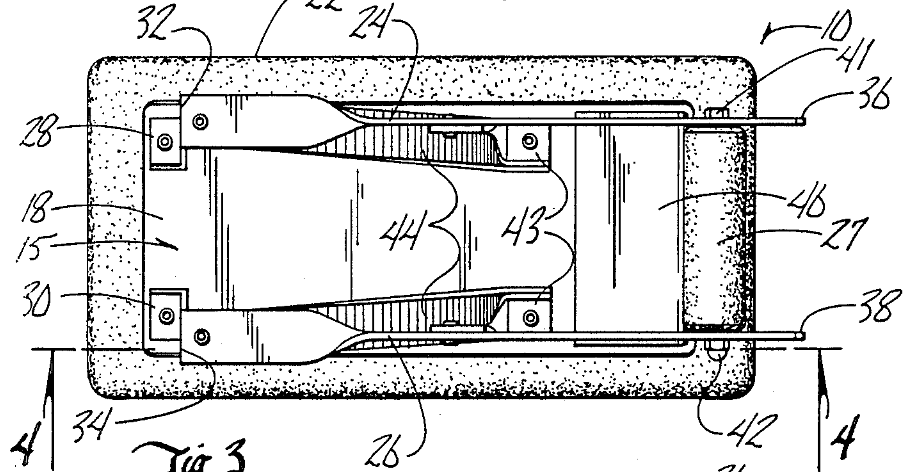
FIG. 3 is a plan view of one of the support plates.

When it is desired to provide traction along the long axis of the spine, away from the head and neck, the patient simply lies in bed or on the floor, as depicted in FIG. 2. The patient then applies force by his arms downwardly and away from the head and neck against the hand grips 27. As a result, there is decompression of the spine and stretching or traction forces applied roughly equal to the force exerted by the patient's arms. If the patient desires less traction he simply eases up on the arm pressure. On the other hand, if the patient desires more traction, he simply increases the arm pressure. The padding 22 provides comfort and prevents any sharp portions of the support plate from potentially causing harm to the patient's body. Likewise, the padding on hand grip 27 provides comfort.

The angle of position of hand grip support straps 24 and 26, as best depicted in FIG. 4, is intentionally provided in order to transmit the forces applied by the arms downwardly against the thigh and to prevent the tendency of the holsters to rotate using the connection between the belt or waist strap 48 and the waist strap clip 46 as a pivot point. Such rotational tendency was found to be present if straps 24 and 26 are parallel to surface 15. This tendency is undesirable.

It therefore can be seen that this device provides a comfortable, inexpensive, home traction device. It is simple of manufacture, easy of use and allows for easy patient adjustment, both from the standpoint of different size of patients, and as well from the standpoint of the amount of traction pressure provided.

It thus can be seen that the device accomplishes at least all of its stated objectives.

Some changes may be made in the construction and the arrangement of this traction device without departing from the real spirit and scope of the invention. It is intended that this invention cover such modified forms of structure and use of mechanical equivalents which may be reasonably included within their scope.

What is claimed is:

1. A traction device for application of stretching traction to a patient's back, comprising:

a pair of plates having an inner surface adapted for engagement with opposite sides of the patient's body adjacent the thighs and an outer surface;

a hand grip rigidly mounted on said outer surface of each plate for grasping by a patient's hand with his arms at his side and application of pressure in an axial direction along the spine and away from the patient's neck by the patient's arms and hands; and means associated with each of said plates for holding a waist strap.

2. A traction device of claim 1 wherein the inner surface of said plates is padded.

3. A traction device of claim 1 wherein said device includes a waist strap extendable around the patient's waist and retained by said means for holding a waist strap on each of said plates.

4. The traction device of claim 1 wherein said hand grip is supported in a manner which transmits downwardly applied pressure to the lower thigh without causing rotary force to be supplied to said plate.

5. The traction device of claim 1 further comprising a pair of hand grip supports for each plate, each having a lower end and an upper end, and which are mounted to said outer surface of each of said plates at said lower end and mounted to said grips at said upper end.

6. The traction device of claim 1 wherein said grips are padded.

7. The device of claim 5 wherein said grips are adjustable along said grip supports.

8. The device of claim 5 wherein each of said grip supports includes a bend between said upper and lower ends, the upper end of said supports being spaced from said plates and said bend being spaced further from said plates than said upper ends of said supports to control pressure transmission along the supports.

9. The device of claim 5 wherein said supports include support legs extending from said grip supports to said plate.

* * * * *